United States Patent [19]

Holtkamp, Sr.

[11] Patent Number: Plant 6,480

[45] Date of Patent: Dec. 20, 1988

[54] AFRICAN VIOLET PLANT NAMED NASSAU

[76] Inventor: Reinhold Holtkamp, Sr., Werther Strasse 112, D4294 Isselburg, Fed. Rep. of Germany

[21] Appl. No.: 21,788

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Nassau characterized by its single, violet-blue flowers; strong, upright flower stems that curve toward the center to form a bouquet above the leaves, profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Nassau.

The new cultivar was referred to during the breeding and selection process by the designation H 77/28, and is a product of a planned breeding program. The new cultivar was originated from a cross made by me in the controlled breeding program in Isselburg, Federal Republic of Germany. The female, or seed parent, was a cultivar designated D 198/5 Blue Single. The male, or pollen parent, was a cultivar designated GG 18 Light Blue Star.

Nassau was discovered and selected by me in 1983 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Nassau has not been observed under all possible environmental conditions. The phenotype may vary significantly with variations in environment such as temperature, light intensity and day length. The following observations, measurements and values describe the new cultivar as grown in Haffen, Federal Republic of Germany and Nashville, Tenn., under greenhouse conditions which closely approximate those generally used in commercial practice.

The following traits have been repeatedly observed and are determined to be basic characteristics of Nassau which in combination distinguish this African violet as a new and distinct cultivar:

(1) Strong, upright flower stems curving toward the center.

(2) First flash of flowers forms a tight bouquet above the leaves.

(3) The flower head builds in three visible, incremental steps that flower 14 days apart.

(4) Profuse flowering.

(5) Each plant carries up to 10 and more upright flower stems, each of which carries 8–12 flowers which are violet-blue in color.

(6) Vigorous grower, compact.

(7) Plant saleable 9–10 weeks after potting.

(8) Dark green velvet leaves, slightly hairy.

(9) Long-lasting, non-dropping single flowers.

(10) Seed capsule pushes slightly through.

(11) Dark brown flower stems.

(12) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight conditions at approximately 2:00 p.m. in Nashville, Tenn.

Botanical classification: *Saintpaulia ionantha,* Ramat., cv. Nassau.

Parentage:

*Male parent.*—GG 18 Light Blue Star.

*Female parent.*—D 198/5 Blue Single.

Propagation: The new cultivar holds its distinguishing characteristics through successive propagations by leaf cuttings.

Plant: From 7 cm to 10 cm tall when grown in pots, and approximately 22 cm in diameter when fully grown.

*Leaves.*—General form: Round to heart-shaped. Diameter: 60–65 mm. Texture: Leatherlike. Aspect: Velvet, slightly hairy. Veins: Underside, well-pronounced, ivy green, shiny with purple between the veins. Color (upper side): Yellow green 147A. Color (under side): Greenish purple with yellow green 145D, partly purplish. Petiole: Strong, brownish purple, hairy.

*Flowers.*—Buds: Bell-shaped, 5–7 mm before opening. Sepals: Five (5) spear-shaped, hairy. Calyx: Shape: Funnel-shaped. Aspect: Spear-shaped, hairy. Peduncle: Character: Strong, upright, hairy. Color: Brownish. Individual flowers: Size: 35–40 mm. Shape: Single, violet-shaped. Color (upper side): Between 94B and 94C. Color (under side): 94C. Borne: Each flower stem carries 8–10 and more flowers on strong, slightly curved, wirelike peduncles that extend above the leaves. The bouquet is attractive and somewhat loose. Flowering habit: Flowers 8–9 weeks after potting.

*Reproductive organs.*—Stamens: 2. Anthers: 2 with 4 anther cells. Filaments: 5 mm. Pollen Color: Yellow 7A. Styles: 6 mm, dark purple.

*Roots.*—Normally developed, white when young turning slightly brownish when older.

Disease resistance: Good.

General observations: Nassau is a vigorous but compact growing variety, with attractive, velvety, medium-green leaves that are slightly shiny. Out of the center, 10 and more strong flower stems appear, slightly bending toward the center, each of which is carrying 8–12 and more single flowers. The flowers are violet blue. Approximately 9–10 weeks after potting the plant is saleable. The flowers are long-lasting and non-dropping and the seed capsule pushes through.

I claim:

1. A new and distinct cultivar of African violet named Nassau, as described and illustrated, and particularly characterized by its single, violet-blue flowers; strong, upright flower stems that curve toward the center to form a bouquet above the leaves, profuse flowering, vigorous growth habit, flowering 9–10 weeks after potting, and its long-lasting and non-dropping flowers.

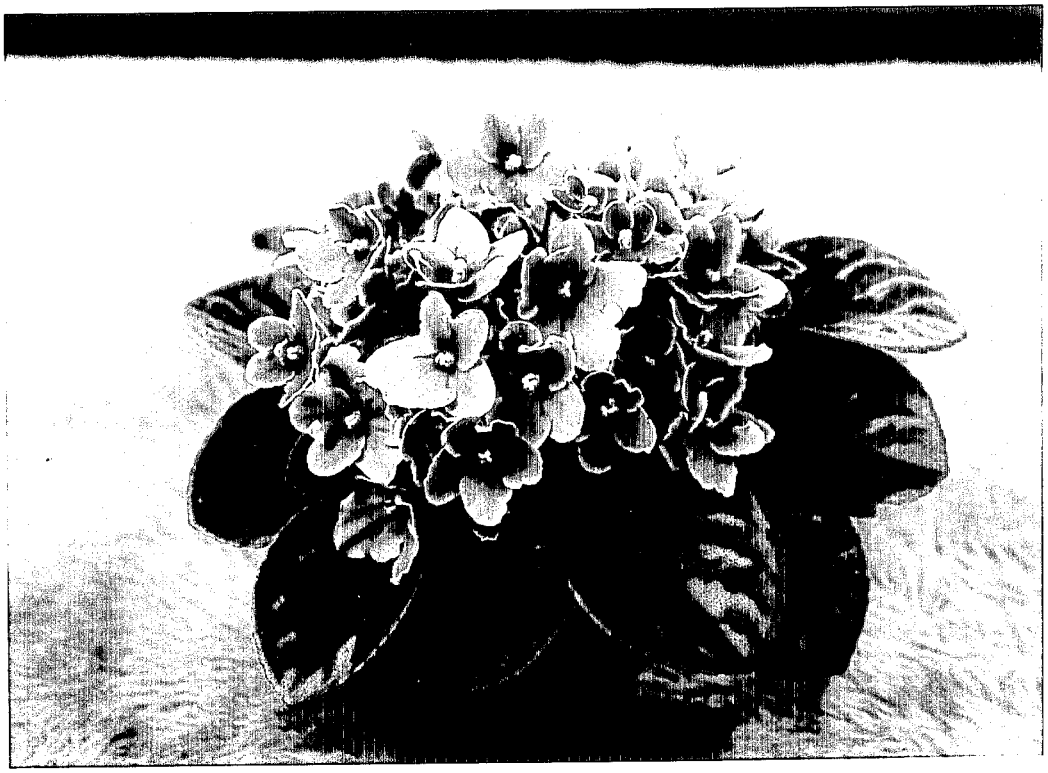

* * * * *